Figure 1:
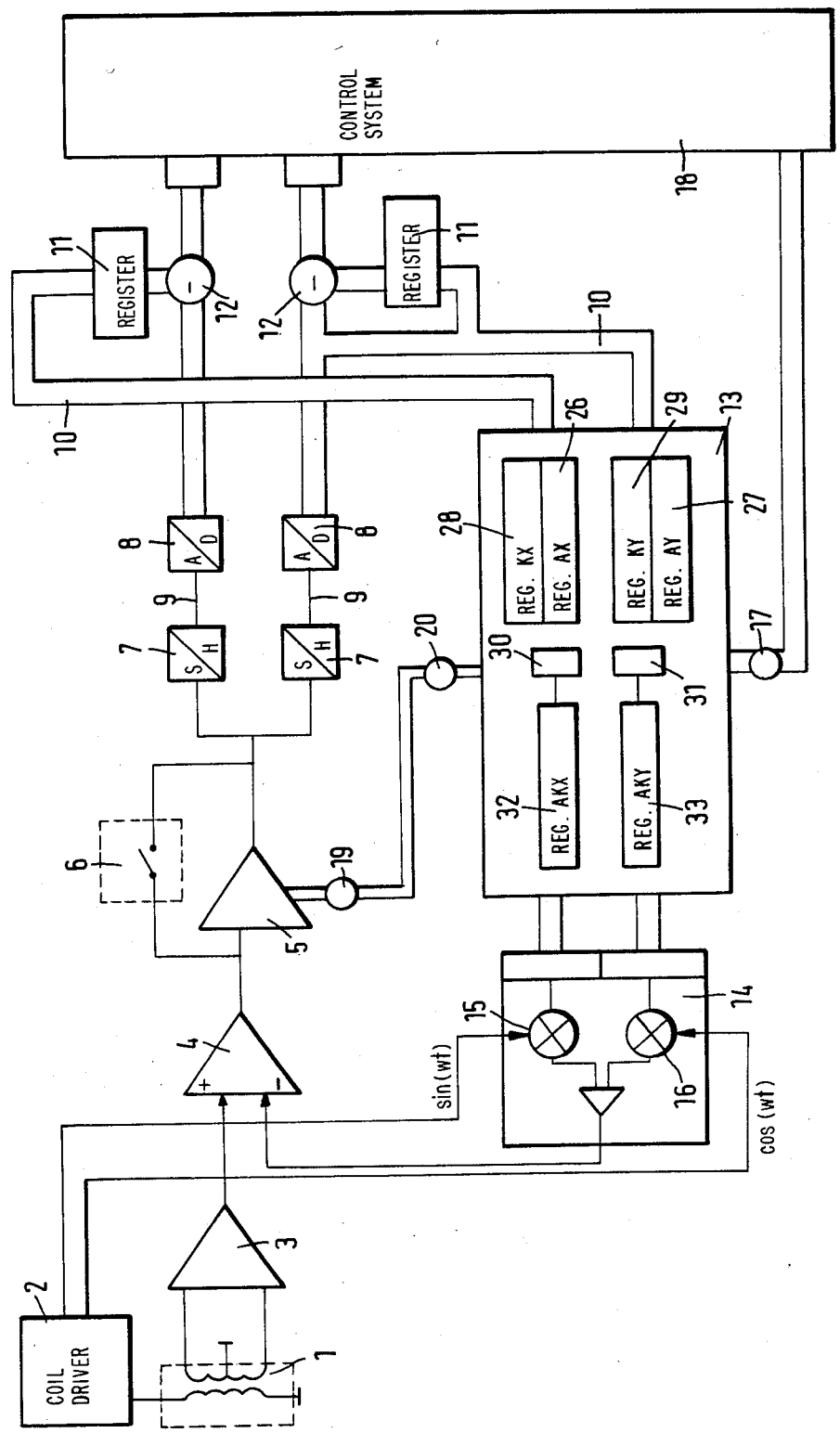

United States Patent [19]

Hüschelrath et al.

[11] Patent Number: 4,564,809
[45] Date of Patent: Jan. 14, 1986

[54] EDDY CURRENT TEST METHOD WITH DEGREE OF AMPLIFICATION SELECTED IN ACCORDANCE WITH A COMPENSATION SIGNAL

[75] Inventors: Gerhard Hüschelrath, Laufach-Frohnhofen; Klaus Abend, Büdingen; Ursula Orthen, Hanau, all of Fed. Rep. of Germany

[73] Assignee: Nukem GmbH, Hanau, Fed. Rep. of Germany

[21] Appl. No.: 390,964

[22] Filed: Jun. 22, 1982

[30] Foreign Application Priority Data

Jun. 30, 1981 [DE] Fed. Rep. of Germany ....... 3125732

[51] Int. Cl.[4] .................... G01N 27/90; G01R 33/12
[52] U.S. Cl. .................................. 324/225; 324/232; 324/233; 324/240
[58] Field of Search ................ 324/225, 232–234, 324/239–243

[56] References Cited

U.S. PATENT DOCUMENTS

| | | | |
|---|---|---|---|
| 4,237,419 | 12/1980 | Törnblom et al. | 324/225 |
| 4,303,885 | 12/1981 | Davis et al. | 324/225 X |
| 4,322,683 | 3/1982 | Vieira et al. | 324/225 |
| 4,326,166 | 4/1982 | Pigeon et al. | 324/225 |
| 4,331,920 | 5/1982 | Kalisch et al. | 324/225 |

*Primary Examiner*—Gerard R. Strecker
*Attorney, Agent, or Firm*—Cushman, Darby and Cushman

[57] ABSTRACT

A method and an instrument for testing materials using the eddy current principle, at different frequencies depending on the output quantity of a coil system, compensation values are generated being typical of interfering factors. These compensation values are subsequently superposed on the output values in order to remove the influence of the interfering factors on the measuring. In this manner with a favorable setting of the working point of an amplifier charged with the output values, an overmodulation is avoided and the dynamic range of the amplifier optimally utilized. Therefore good measuring results can be obtained even if the percentage of the interfering signals as compared to the signal controlling the detecting of defects, is relatively high.

4 Claims, 6 Drawing Figures

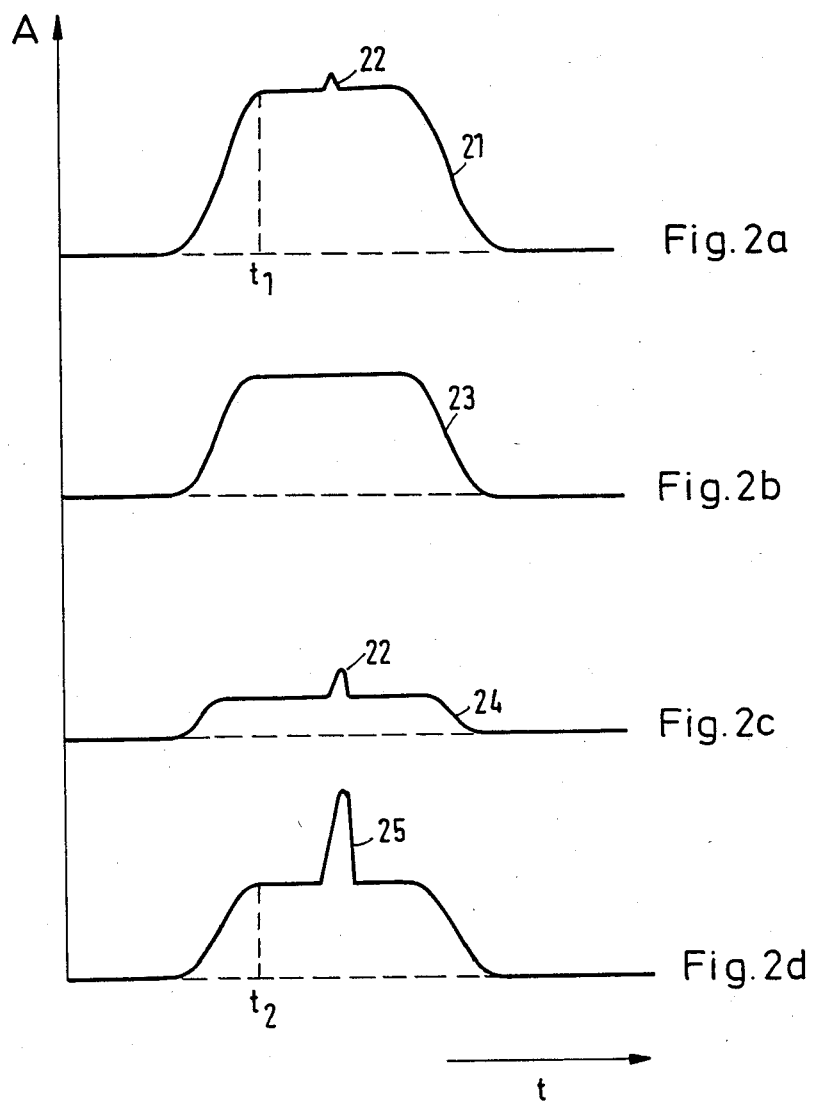

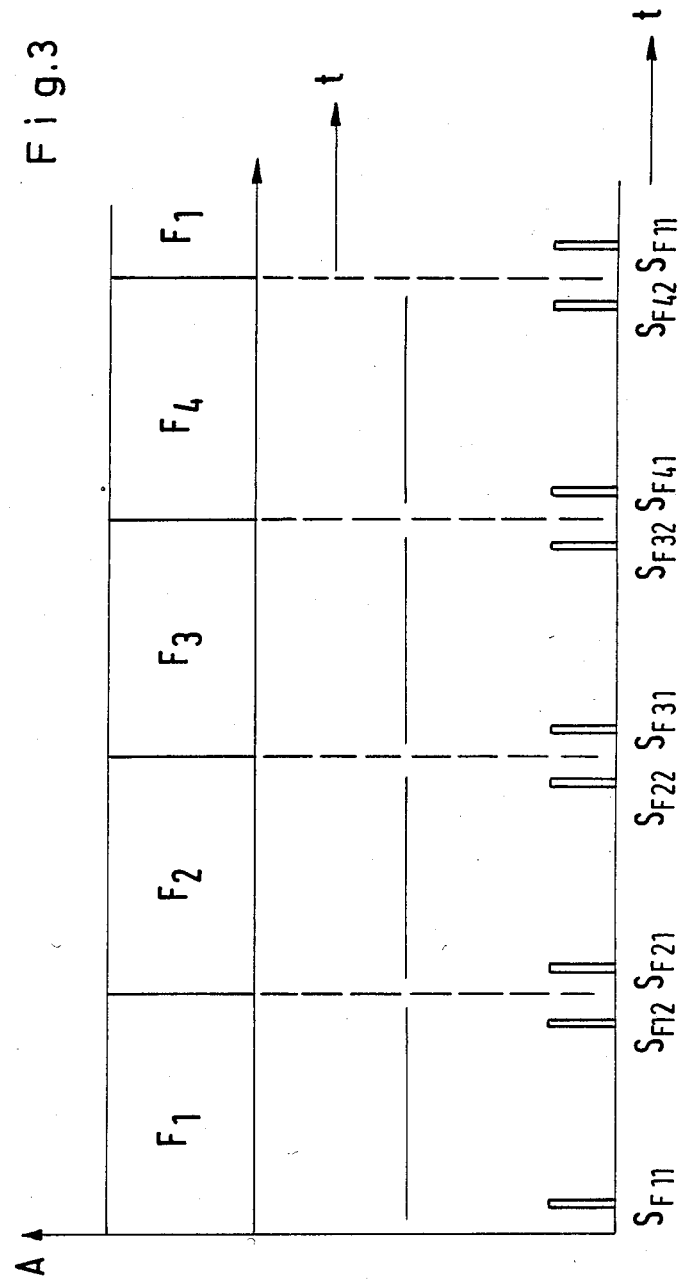

EDDY CURRENT TEST METHOD WITH DEGREE OF AMPLIFICATION SELECTED IN ACCORDANCE WITH A COMPENSATION SIGNAL

This invention relates to a method and an instrument for testing materials using the eddy current principle, by which a coil moved in relation to a test piece, is generating magnetic alternating fields with alternatively different frequencies, inducing eddy currents in the test piece, which will produce a secondary field in the coil or a tracer coil, where the output rate of the coil or, resp. tracer coil is divided in its real and imaginary portions.

Such a method is described in the German Disclosure No. 27 39 873. By this method one can obtain quantitative data on quality characteristics of the test pieces. The phase angle and the amplitude of the potential induced in the coil by the secondary field are dependent on the magnetic coupling and the properties of the respective test object. Thus one can determine dimensions, interval changes, the conductivity, structural condition, alloying differences, as well as cracks in the test pieces. By this known method the different frequencies are successively fed to the coil. The real and imaginary portions are determined frequency-serially. The output quantity of the coil, following an amplification, is fed to a first multiplier for extracting the real portion, and to a second multiplier for extracting the imaginary portion. In the first multiplier the output quantity is multiplied by the sine of the test signal. The cosine signal, phase-displaced for 90°, is fed to the second multiplier. The multipliers each are connected to low-pass filters with which compensating systems are connected, by which undesired test parameters are removed while selected test parameters are preserved.

There is also known an instrument for testing eddy currents, where test coils and transmitters for the emission of output quantities are arranged in an impedance bridge (German Disclosure No. 30 22 078). With this instrument the testing frequencies are simultaneously fed to the coils. In order to frequency-wise separate the components of the output quantity, band filters are provided, each being series-connected to summation amplifiers. The summation amplifiers are fed at one input thereof with the output quantity and at the other input thereof with balancing signals, by which certain frequencies in the output quantity are deleted. The band filters are feeding amplitude detectors, to which a mixer is connected removing the undesired signal parameters.

It is the object of the invention to develop a method and an instrument of the kind as described at the outset in such a manner that in spite of existing interfering signals of a high signal level, in the case of a signal of a lower signal level being important for the detection of defects, an overmodulation of the input amplifiers at a high amplification factor is avoided and the amplitude range is utilized as far as possible.

According to the invention this object is realized in that dependent on the output quantity appearing at the respective frequency, a compensation quantity is generated, which subsequently is superimposed on the output quantity and coupled to an amplifier for setting its working point for the purpose of an optimal utilization of the amplitude range of the amplifier.

Hereby it is possible to measure accurately even at big differences of level in the output quantity of the coil. For example, interfering effects like the raising-off effect or ferritic inclusions will generate much higher signal levels than cracks in the test piece will do. However, for security reasons cracks very often must be detected even at rather small dimensions. On increasing the amplification to detect small useful signals being superposed on interfering signals with higher levels, the amplifiers charged with the output quantity are frequently overmodulated. Then it is no longer possible to make out small signals as they are caused by cracks. This disadvantage is removed by the above mentioned method for the dynamic compensation of interfering influences.

A preferred embodiment of the present invention provides an arrangement for testing a workpiece wherein a coil generating an alternating magnetic field is moved with respect to the workpiece so as to induce an eddy current therein which in turn induces a secondary field in the coil or in a tracer coil. The testing method includes the steps of deriving a testing signal from the secondary field; dividing the testing signal into real and imaginary components thereof; generating real and imaginary compensation values; and utilizing these real and imaginary compensation values to control the degree of amplification of an amplifier for amplifying the testing signal so that the amplifier will always operate within its dynamic range.

In an advisable embodiment the coil is arranged above a spot of the test piece being free from material disturbances, subsequently the output quantity of the test piece is measured and the real portion and the imaginary portion are stored as reference values for the balancing of a test coil. Hereby the characteristic values typical for a reference coil are determined, which will be available for subsequent measuring processes. The eddy current testing apparatus during these measuring operations can then work in absolute or key-coil operation without requiring any additional coil for the generation of the reference values.

An instrument for testing materials after the eddy current principle with a coil being moved relative to a test piece, which coil can be charged with different frequencies, as well as with an amplifier series-connected to the coil or, resp. feeler coil, to which amplifier being connected an arrangement generating the real and imaginary portions of the output quantity of the coil, this arrangement being connected to a compensation connection, for carrying out the above described method is designed according to the invention in such a manner that between the coil or, resp. the feeler coil and the amplifier there is arranged a compensation amplifier having two inputs; that to the amplifier having the variable amplification there are connected scanning and holding connections, each being connected via analog-digital converters with a data bus, to which there are connected storage units for the neutral point correction, adding and subtracting units and inputs of a register, of which further inputs are connected with a controller unit, having outputs connected to the control input of the amplifier and with a vector generator, of which the output is connected to the second input of the compensation amplifier.

In a preferred embodiment there are provided in the computer system one register each for the storage of the basic compensation values coordinated to the real or, resp. imaginary portion of the output quantity, and one register each for the storage of the real or, resp. imaginary portion of the respective measuring device, where the registers coordinated with the real portions and those coordinated with the imaginary portions are each connected to adding/substracting connections, followed in series-connection by one register each for the storage of results, and where the outputs of these registers are connected with the inputs of the vector generator. This arrangement enables a quick production of the compensation value. The basic compensation values can also include factors being required for the compensation of errors caused by the instrument.

Preferably the outputs of the adding/subtracting mechanisms are connected with the control system.

In a preferred embodiment the control mechanism includes a micro computer with a data and a program storage.

Further preferred embodiments are described in the following claims.

In the following the invention is explained in more detail by means of an embodiment example shown in the attached drawing, from which further details, characteristics and advantages will result.

FIG. 1 shows a block wiring diagram of an instrument for testing materials after the eddy current principle, FIGS. 2a to d are time diagrams of different signals appearing in the instrument according to FIG. 1, FIG. 3 is a time diagram of the scanning times and the transition times of the compensation quantities at different frequencies.

A coil system 1, which can be an absolute, difference, or feeler-sonde coil, is connected with a coil drive 2, by which different frequencies are generated successively with respect to time. The measuring coil (not shown in any further detail) is connected to a differential amplifier 3, which is feeding one input of a compensation circuit provided with two inputs. Preferably the compensation circuit is a differential amplifier 4 having one non-negating and one negating input. Connected to the differential amplifier 4 is a further amplifier 5 being intended for the main amplification. The amplifier 5 includes a feedback circuit 6 that can be connected if so desired. With the output of the amplifier 5 there are connected the inputs of two sample and hold circuits 7, each of which is series-connected to an analog-digital converter 8 via the lines 9. The outputs of the analog-digital converters 8 each are connected to a data bus 10. Connected to the respective data buses 10 are further registers 11 and inputs of arithmetic units 12. Each bus 10 further is feeding parallel inputs of an arithmetic unit 13, including (not shown) registers, adding/subtracting units and switching arrangements for squaring and evolution.

Two rows of parallel outputs (not shown in any further detail) of the arithmetic unit 13 are connected with inputs of a vector generator 14, which at first converts the digital compensation values indicated by the arithmetic unit 13 into analog values and then leads these values in two channels to multipliers 15, 16. In the first multiplier 15 one of the analog compensation values is multiplied by a signal corresponding to the sine of the driver signal of the coil. In the second multiplier 16 the other supplied compensation value is multiplied by a signal corresponding to the cosine of the driver signal of the coil. The output signals of the multipliers 15, 16 are superimposed and subsequently led to the inverting input of the differential amplifier 4 as an analog compensation value. Other inputs 17 of the arithmetic unit 13 are connected to a control system 18, to which the outputs of the computing system 12 are likewise connected. The computing systems 12 are adding/subtracting connections.

The amplifier 5 has control inputs 19 for changing the amplification factor. The inputs 19 are connected to outputs 20 of the arithmetic unit 13, series-connected to which is an arrangement in the arithmetic unit 13 forming the square root from the sum of the squares of the input data. The control system 18 includes a micro-computer (not shown in any detail) being provided with a data and a program storage mechanism. The sample and hold circuits 7, the analog-digital converters 8, the registers 11 and the computing systems 12, like the computing system 13 are operating under control of the control unit 18. The respective control lines, however, are not shown in FIG. 1.

The arithmetic unit 13 includes registers 26 and 27, being used for the storage of the real portion and the imaginary portion of the respective value measured each time. The registers 26 and 27 are fed by the analog-digital converters 8 via the after-connected data bus lines. In FIG. 1 the function of the registers 26, 27 respectively is indicated by the symbols AX and AY. The letters X or, resp. Y identify the real, or resp. imaginary portion of the quantity to be measured indicated by A.

Two further registers 28, 29 of the computing unit 13 serve as receivers of basic compensation values. The registers 28, 29 each are likewise connected to a data bus 10 each. The basic compensation values concern constant values belonging to each measurement, which also include factors compensating measuring errors due to the respective instrument. The storge of constant compensation quantities is indicated in FIG. 1 at the registers 28, 29 by the letter K, while the coordination to the real or, resp. imaginary portion is indicated by X or, resp. Y. Each pair of registers 26, 28 or, resp. 27, 29 coordinated to the real or imaginary portions is connected to an adding/subtracting connection 30 or, resp. 31. In the connections 30, 31 the input values are added sign-correctly. Connected after the adding and subtracting connections 30, 31 each time are registers 32, 33, in which the result of the addition is stored. To identify their functions, the registers 32, 33 are designated in FIG. 1 by the letters AKX and AKY. The outputs of the registers 32, 33 are feeding inputs of the vector generator 14.

The arrangement provided in the arithmetic unit 13 (not shown in any further detail) intended for the calculation of the square root of the sum of the squares of the input data is fed by the registers 32 and 33.

The inputs 17 are connected to the registers 32, 33. Therefore the registers 32, 33 can alternatively receive data from the connections 30, 31 or from the control system 18.

The output factor of the coil system 1, in analog form is applied to the inputs of the sample and hold circuits 7, via the differential amplifier 3, the differential amplifier 4 and the main amplifier 5. The output signals of the amplifier 5 are divided in their real and imaginary portions by measuring the sine and cosine components at set times. The real portion and the imaginary portion each are fed to one of the sample and hold circuits 8. After conversion into digital values, the real portion and the imaginary portion each are present on a data bus 10 each. In the registers 11 there are included balancing factors, which are subtracted from the actual measuring values prior to being further processed by the control unit 18, in order to single out the respective parameter being of interest at the moment from these parameters not being of interest.

As long as the input signals on the differential amplifier 3 and the series-connected amplifiers do not oscillate over a further level range, an exact measuring of the test body can be obtained in the above explained manner even without any compensating factors.

Very often the output signals of the coil system 1 include a high percentage of interfering signals, while the signal portion relevant to the respective measuring of the properties of the test body has a small level only. This can be seen with the aid of FIG. 2a. An interfering signal 21 with high level is superposed by a useful signal 22 with small level. Interfering signal levels of the kind as shown in FIG. 2a are caused e.g. by the raising-off effect, by ferritic inclusions in the test body, etc. These disturbing signals are more distinct than e.g. the useful signal 22 produced by a crack in the test piece. The behaviour of the signal as shown in FIG. 2a appears for example at one of the frequencies intended for the testing, to which specific frequency gates, i.e. periods, are coordinated. At the beginning of the frequency gate after the damping of the transient phenomena during a period $t_1$, the computing unit determines the level of the interfering signal 21. The real portion and the imaginary portion of the interfering signal are stored in the registers 26, 27 of the arithmetic unit 13 and thereafter are added up with stored constants correctly to sign. These constants typical for a certain measuring method are fed to the registers 28, 29 of arithmetic unit 13. The results of this processing of the real portion and the imaginary portion are then led to the registers 32, 33 and as digital data reach the inputs of the vector generator 14, at the output of which the compensating signal is produced as represented by the waveform in FIG. 2b. The temporal process of the compensating signal corresponds approximately to that of the interfering signal 21. By the heterodyning of the compensating signal 23 and the interfering factor 21 in the differential amplifier 4, a screened signal 24 as shown in FIG. 2c is led to the input of the amplifier 5. Superposed to this screened signal is again the useful signal 22. The ratio of useful/interfering signal is by far more favorable at the behaviour of the input signal of the amplifier 5 as shown in FIG. 2c than that of the behaviour curve shown in FIG. 2a. By providing the difference of the output of coil system 1 and compensating signal one obtains a favorable working point of the amplifier 5. Besides the risk of overmodulation of the amplifier 5 will be avoided. After an overmodulation no crack signals could be made out anymore.

Thus digital compensation values will be obtained from the real and imaginary portions of the interfering signal. These compensation factors or values being proportionate to these compensation factors will be squared and summed up. By extracting the root of this sum of the squares there will result a control factor for the control input 19 of the amplifier 5. In dependency on the digital compensation values, the amplification is set so high that the value range for the signal levels presenting themselves during the measuring at the output of the coils is optimally utilized. Therefore, at the output of the amplifier 5 the signal with a high useful signal 25 as shown in FIG. 2d is generated, corresponding to a defect in the test body. Via the sample and hold circuits 7 and the analog-digital converters 8, a higher defect signal value is thus determined when there is a defect in the test body. Therefore more places will be available for the digital values of the real and imaginary portions in the binary words issued by the analog-digital converters.

Supposing the coil drive 2 is generating four different frequencies during four consecutive periods. These frequencies are shown as frequency gates along the x-axis of a system of coordinates in FIG. 3, of which in the axis of ordinates amplitudes are schematically shown. The frequency gates are marked F1, F2, F3 and F4.

At the beginning of each frequency gate, the arithmetic unit 13 is supplied by a test value of the output factor of the coil system 1. The times of providing of the test values are shifted approximately towards the time of switching-on of the respective frequency gate. In FIG. 3 the times for the taking-over of the test values in the computing system for the different frequency gates are marked $S_{F11}$, $S_{F21}$, $S_{F31}$, and $S_{F41}$, respectively. After storing the test values, arithmetic unit 13 determines the compensation factors applicable to the respective frequency and adjusts the amplification degree of the amplifier 5 accordingly. Problems with transients virtually will arise at the shortest frequency gate only. This can be e.g. 40 $\mu$sec. It is possible to use arithmetic unit 13, requiring approx. 5 $\mu$sec for the necessary computations and the data transport. Therefore, for the measuring with the compensation factors around 30 $\mu$sec are left over at the shortest frequency gate. This period is sufficient since the flow of eddy currents is not influenced by the processes in the control system 18.

The frequency gates $F_1$, $F_2$, $F_3$, $F_4$ are only of short duration. Therefore the measuring values sampled at the time points $S_{F11}$, $S_{F12}$, $S_{F21}$, etc. are locally and temporally virtually invariable. The waveform of the output signal as shown in FIG. 2 is measured by means of several groups of frequency gates $F_1$, $F_2$, $F_3$, $F_4$. Supposing that the point $t_1$ according to FIG. 2a is coinciding with the sampling time point $S_{F11}$, then the sampling time point $S_{F11}$ results e.g. at a time point $t_2$, which in reference to the duration of the waveform shown in FIG. 2 is following after the time point $t_1$ at a short time interval.

If the amount of the defect just to be measured is predetermined, then the duration of the frequency gates $F_1$, $F_2$, $F_3$, $F_4$ and the succession of the groups of frequency gates must be adjusted to the relative speed by which the coil system 1 is moved along the test piece. Thereby several groups of frequency gates should scan the part corresponding to the smallest defect to be registered. Due to the high frequencies of the frequency gates, e.g. a group of four frequency gates can claim only 1 msec, so that the relative motion between coil and test piece occurring during the scanning process will be negligible only. An influence on the measuring caused hereby can therefore be neglected.

The values determined during the sampling times $S_{F11}$, $S_{F21}$, $S_{F31}$ and $S_{F41}$ are used for producing the compensation factor. The output signals of the analog-digital converters 8 are therefore fed to arithmetic unit 13. Measuring values obtained at the sampling times $S_{F12}$, $S_{F22}$, $S_{F32}$, and $S_{F42}$, via the arithmetic units 12 are led into the control system 18, in which they are processed or, resp. evaluated for the defect registering.

Supposing that the interfering signal 21 has a maximum height of approx. 3 volts, it is measured during the periods $S_{F11}$, $S_{F12}$, $S_{F13}$, and $S_{F14}$ with a tolerance of ±200 mV and processed in the arithmetic unit 13, which produces a compensation factor and a setting value for the amplification factor. The amplification factor is set on the amplifier 5 and transmitted to the control system 18. Each time at later time points $S_{F12}$, $S_{F22}$, $S_{F32}$, $S_{F42}$, during the frequency gates $F_1$, $F_2$, $F_3$, $F_4$, the control system takes over the measured quantities and adds the matching compensation value within the range of the places of higher valency of the data words.

By arithmetic unit 13 and the vector generator 14 one can preferably reproduce a reference coil. Thereby the typical characteristics for such a reference coil are stored in the arithmetic unit 13 and during the measuring process are fed to the inputs of the vector generator 14. In this manner the eddy current testing apparatus can be operated with absolute coils or scanning coils without requiring an additional coil for the reference. Consequently there will also be no more high expenses being otherwise necessary due to the great demands made upon the mechanic and technical constancy of the reference coil. The imitation of the reference coil by the arithmetic unit 13 and the vector generator 14 supplies measured values of the same accuracy as they are obtained with a reference coil of high mechanic and thermic constancy.

The determination of the characteristic values takes place by the measuring of the output signal of the coil 1 over a point on the surface of the test piece being free from material disturbances. The output quantity of this measuring, divided in the real and the imaginary portion, is filed in the control system 18. The characteristic values serve as further compensation values in the absolute or scanning coil operating method.

In the control system 18, especially in the storage of the micro-computer, the values obtained at the measuring of a test body can be stored, which values being very exact due to the wide dynamic range. These values are still available for subsequent measurings on test pieces. Therefore evaluating equality of parts may be made by using data measured at a later time with those values initially obtained with a heat body, where the control system 18 will lead the stored values as reference values to the connections 17. Thus a very exact comparison can be made.

There is also a possibility to deposit the measured quantities obtained from the measuring at the different places of a test body, according to their respective locations, in the control system 18 or, respectively in the storge unit of the microcomputer. At repetition tests, the control system 18 will supply the respective values, likewise according to the location, to the inputs 17 of arithmetic unit 13 as reference values. Therefore it is possible to detect the differences existing in the different test pieces with a high degree of accuracy.

Very often the test body presents regular variations of its surface. These can be e.g. chatter marks of tools. Also tube ends of single tubes pieced together on their front faces, like the chatter marks, will cause a defect indication, even though no real defects are concerned.

These undesired defect recordings caused by such variations can be removed in that the control system 18, via the connections 17, will transmit respective compensation values to the arithmetic unit 13. Thereby the control system 18 serves as a time-lag element and supplies the compensation values synchronously to place and time to arithmetic unit 13, which via the vector generator 14 is producing a compensation signal by means of which the interfering signal portions in the resulting signals are removed.

We claim:

1. In a workpiece testing system wherein a coil generating an alternating magnetic field is moved with respect to a workpiece so as to induce eddy currents therein which eddy currents produce a secondary field which induces a potential in said coil or in a tracer coil, a method for testing said workpiece comprising the steps of:

deriving a reference signal from said secondary field by positioning the coil above a place on said workpiece that is substantially defect free;

superimposing on said reference signal an error correcting signal to cancel any unbalance that may exist due to interfering signals associated with measuring equipment;

generating, in response to said superimposed signal, a compensating signal;

testing the workpiece by moving said coil relative thereto and providing a testing signal derived from said secondary field;

superimposing said compensation signal on said testing signal; and amplifying said superimposed signals with an amplifier, the degree of amplification of said amplifier being selected in accordance with the level of said superimposed signals to amplify within the dynamic range of the amplifier.

2. A method according to claim 1, further including the steps of:

dividing said reference signal into real and imaginary components thereof;

superimposing said real and imaginary components on real and imaginary components, respectively, of the error correcting signal; and utilizing said superimposed real and imaginary components to control the degree of amplification of said amplifier.

3. A method according to claim 1 further including the step of storing said real and imaginary components of the reference signal for use at a later time in analyzing said testing signal.

4. A method according to claim 3 further including the step of storing said real and imaginary components of the reference signal for use at a later time in analyzing said testing signal.

* * * * *